(12) United States Patent
Pope et al.

(10) Patent No.: US 9,510,599 B2
(45) Date of Patent: Dec. 6, 2016

(54) DAZOMET COMPOSITIONS

(71) Applicant: Osmose Utilities Services, Inc., Buffalo, NY (US)

(72) Inventors: Thomas Pope, Newnan, GA (US); Douglas J. Herdman, Fayetteville, GA (US); Peter Tham, Jonesboro, GA (US)

(73) Assignee: OSMOSE UTILITIES SERVICES, INC., Buffalo, NY (US)

( * ) Notice: Subject to any disclaimer, the term of this patent is extended or adjusted under 35 U.S.C. 154(b) by 497 days.

(21) Appl. No.: 13/950,773

(22) Filed: Jul. 25, 2013

(65) Prior Publication Data
US 2015/0030501 A1    Jan. 29, 2015

(51) Int. Cl.
*A01N 43/88*  (2006.01)
*B27K 3/34*   (2006.01)
*B27K 3/50*   (2006.01)

(52) U.S. Cl.
CPC .............. *A01N 43/88* (2013.01); *B27K 3/343* (2013.01); *B27K 3/50* (2013.01)

(58) Field of Classification Search
CPC ..................................... A01N 43/88
See application file for complete search history.

(56) References Cited

U.S. PATENT DOCUMENTS

| | | | | |
|---|---|---|---|---|
| 2005/0090402 A1* | 4/2005 | Dieing | ................... | A01N 25/10 504/361 |
| 2015/0289503 A1* | 10/2015 | Abrey | ................... | A61K 47/10 504/359 |

OTHER PUBLICATIONS

"Hazardous Substance, Non-Dangerous Goods: Preschem Polesaver Rods & Bioguard," Preschem Pty Ltd, Issue No. 010, pp. 1-6, May 2005.

"Polesaver Rods," Preschem Pty Ltd, pp. 1-4, printed Mar. 18, 2014 (http://preschem.com/products/wood-pole-preservatives/polesaver-rods/).
"Preschem Polesaver Rods (PS10): Technical Data Sheet," Preschem Pty Ltd, Issue No. 005, pp. 1-2, Oct. 2004.
"Remedial Timber Treatment Products," Preschem Pty Ltd, pp. 1-5, printed Mar. 18, 2014 (http://preschem.com/products/wood-pole-preservatives/).
K. Platt, "Polesaver Rods Stop The Rot," BusinessTimes, No. 21, pp. 1-5, Mar. 2012, posted Nov. 29, 2012 (http://businesstimes.net.au.s129689.gridserver.com/articles/polesaver-rods-stop-the-rot/).
"Fumigant Treatment for Utility Pole Projections," Osmose Utilities Services, Inc., 2005.
Gross, et al., "Dazomet: A Review of an Efficacious, Safe and Cost-Effective Fumigant for Wood Poles," retrieved from the internet on Nov. 14, 2013 (http://www.poles.com/online/templatemedia/all_lang/resources/DAZOMET-EDM+2008+FINAL+030408.pdf).
Morrell, et al., "Oregon State University Utility Pole Research Cooperative 29th Annual Report," Department of Wood Science & Engineering Oregon Wood Innovation Center (OWIC), Oct. 26, 2009.
Leavengood, S., et al., "Oregon State University Utility Pole Research Cooperative 28th Annual Report," Department of Wood Science & Engineering Oregon Wood Innovation Center (OWIC), Oct. 16, 2008.
Morrell, J. J., et al. "Oregon State University Utility Pole Research Cooperative Department of Wood Science and Engineering Oregon Wood Innovation Center 32nd Annual Report," Oregon State University Utility Pole Research Cooperative, Oct. 16, 2012.

* cited by examiner

*Primary Examiner* — Sean E Conley
*Assistant Examiner* — Donald Spamer
(74) *Attorney, Agent, or Firm* — Troutman Sanders LLP; James E. Schutz; Alexis N. Simpson

(57) ABSTRACT

A solid body of dazomet for use in internal remedial treatments of wood and methods of applying such solid bodies to wooden structures and manufacturing such solid bodies. The solid bodies can be easily transported and inserted into treatment holes in utility poles, wooden pilings, and other wooden structures, delivering a precise, accurate dose of insecticide and fungicide that combats internal decay in the wood.

28 Claims, No Drawings

DAZOMET COMPOSITIONS

TECHNICAL FIELD

The present invention pertains to the protection of wooden structures from internal decay caused by insects, fungi, and other pests. More particularly, the present invention is directed towards a composition and a product for the internal remedial treatment of wood comprising a solid body of the disclosed dazomet compositions and the insertion of a solid body of dazomet into a treatment hole in a wooden structure.

BACKGROUND OF THE INVENTION

Dazomet (Tetrahydro-3,5-dimethyl-2H-1,3,5-thiadiazine-2-thione) is a non-selective fumigant with several uses. Fumigants form gasses after application that have biocidal activity. When dazomet is applied, it is quickly broken down into several active degradation products. The major degradation product formed by dazomet is methyl isothiocyanate (MITC). MITC is highly volatile and is responsible for the fumigant properties of dazomet. In the soil, dazomet exhibits fungicidal, herbicidal and nematicidal properties. Unlike other soil fumigants, dazomet is applied as a dry granule and incorporated into the soil or applied to the soil surface and watered into the soil to activate it. Dazomet is also registered as an algaecidal, bacteriocidal, fungicidal, microbicidal, and mildewcidal agent for use during the production of pulp and paper, treatment for coatings, adhesives, epoxy flooring compounds, slurries, and high viscous suspensions, biocidal treatments in petroleum operations and recirculating water cooling systems and as a remedial treatment of wooden utility structures.

Long-term test results have demonstrated the excellent efficacy of dazomet as a wood pole fumigant. The addition of an accelerant, such as copper naphthenate, increases the release of fumigant early in the treating cycle, thus eliminating concerns from earlier testing that the product was not breaking down fast enough to deliver a lethal dose to the inhabiting fungi.

Diffusible preservatives, often containing boron or fluoride compounds, come in a wide spectrum of different forms, including powders, pastes, gels, thickened solutions, and solid rods. Some diffusible preservative treatments take the form of boron or boron-copper mixtures which are melted and molded into rods. Other diffusible preservative treatments are boron-containing pastes which can be applied to the wooden structure to be preserved and then formed into a desired shape and left to solidify before application.

Several products using dazomet for remedial treatment of wooden utility poles are commercially available. Granular fumigants, such as Osmose's DuraFume®, contain a crystallized solid dazomet fumigant that decomposes to produce MITC. Application of granular fumigants in the field, however, is cumbersome and inefficient. Like liquid fumigants, granular fumigants must be poured into treatment holes pre-drilled from above, and are also subject to spilling and difficulties in accurately measuring the proper dosage of dazomet to be applied. Granular fumigants are also subject to clumping and unwanted dust production. Addition of accelerants, such as copper naphthenate or copper sulfate to granular dazomet in a utility pole leads to inefficient and sub-optimal distribution of the accelerant throughout the dazomet granules.

Although boron- and fluoride-based rods overcome the disadvantages of granular compositions and have been commercially developed, the formulation of dazomet into compressed solid forms has not succeeded in producing a product with sufficient hardness, friability and performance necessary for field use. Oregon State University's Utility Pole Research Cooperative (UPRC) tested a fumigant "rod" containing dazomet that was similar to boron-containing diffusible preservative rods. The UPRC "rods" were prepared by wetting powdered dazomet with water followed by compression into pellets. Water, however, triggers dazomet decomposition to produce the active MITC biocide, during manufacturing. MITC generation prior to application raises is inefficient and potentially hazardous. The UPRC pellets exhibited poor friability and hardness which is unsuitable for commercial applications and normal handling and applications in the field.

There has long been a need in the utilities industry for an alternative to granular dazomet formulations that could possibly eliminate some of the undesirable handling characterizes of a granular formulation. Although a dazomet rod product could fill the market void as a substitute for granular systems, no serious efforts to commercialize them have taken place.

The difficulties in formulating a dazomet rod suitable for commercial applications has resulted in the development of several alternatives to a compressed dazomet rod. In one case, dazomet is packaged into preformed tubes. For example, Super-Fume Tubes have been developed, based on the same effective and safe granular formula that is applied from jugs (HDPE/HDPP Containers). The tubes use a perforated or gas-permeable outermost packaging material to contain a pre-set dose of the granular dazomet product. Another alternative to granular dazomet is Osmose's MITC-FUME®. This product consists of an aluminum tube filled with solid 97% MITC (instead of dazomet) and capped with an air-tight seal.

Compositions of dazomet suitable for formation of solid dazomet bodies, such as rods, that have properties (such as hardness and friability) suitable for use as commercial wood preservative for the internal remedial treatment of wood are disclosed herein. Methods of producing such dazomet compositions and solid bodies and methods for their use in the remedial treatment of wood utility structures, such as wood utility poles, are also disclosed.

SUMMARY OF THE INVENTION

In certain aspects of the invention, a composition comprising a flowable mixture of dazomet (tetrahydro-3,5-dimethyl-2H-1,3,5-thiadiazine-2-thione), a lubricant and a binder. In another aspect of the invention, the dazomet is in the form of granules or powders. In another aspect of the invention, the lubricant is an oil or a hydrogenated oil. In one aspect of the invention, the binder is a carbohydrate, including, monosacharides, oligosaccharides and polysaccharide, including starches, dextrins, maltodextrins, soy flour, dextrose, a polyol or a combination thereof. In another aspect of the invention, the binder is a polysaccharide.

In certain aspects of the invention, the compositions comprise between 80 and 96% solid tetrahydro-3,5-dimethyl-2H-1,3,5-thiadiazine-2-thione, between 0.5 and 5.0% of a lubricant and between 1 and 15% of a binder. In certain aspects of the invention, the compositions comprise between 90 and 96% solid tetrahydro-3,5-dimethyl-2H-1,3,5-thiadiazine-2-thione, between 0.5 and 5.0% of an oil and between 1 and 5% of a polysaccharide. In certain aspects of the invention, the compositions comprise between 90 and 96% solid tetrahydro-3,5-dimethyl-2H-1,3,5-thiadiazine-2- thione, between 0.5 and 5.0% of a saturated oil and between 1 and 5% of a polysaccharide. For example, the hydrogenated oil may be a hydrogenated vegetable oil. The polysaccharide may be a starch, such as maltodextrins.

The compositions disclosed herein are compressed into a solid body to produce a product for the internal remedial treatment of wood. The solid body may take a form selected from the group consisting of a rod, tablet, pellet and a stick. The disclosed products may have a diameter of about 5 millimeters to about 30 millimeters, a length of about 100 millimeters to about 600 millimeters. In one aspect of the invention, the length of the rod is from about 100 millimeters to about 350 millimeters. In one aspect of the invention, the length of the rod is 2.5-times greater than the diameter of the rod. In one aspect of the invention, the product has a weight of between 10 and 500 grams. In another aspect of the invention, the product may comprise an accelerant, such as a compound, including but not limited to copper naphthenate, copper sulfate, copper carbonate, basic copper carbonate, copper hydroxide, cupric oxide, ammoniacal copper, copper-amine complexes, cuprous oxide, copper oxychloride, copper dimethyldithiocarbamate, copper borate or a zinc compound, including but not limited to zinc naphthenate. The accelerant may be in the form of a solid, dissolved liquid or copper particles dispersed in an aqueous or non-aqueous carrier. The product of the invention may be sheathless.

The present invention also provides methods for internal remedial treatment of wood, comprising the steps of inserting the disclosed products into a treatment hole in a wooden structure. In certain aspects of the invention, the wooden structure contains multiple treatment holes, and multiple solid bodies of dazomet are inserted into the multiple treatment holes which may be pre-drilled (before application of the product). In certain aspects of the invention, the disclosed methods of the remedial treatment of wood further comprise the step of boring the multiple treatment holes into the wooden structure. The treatment holes may have diameters of about 5 millimeters to about 30 millimeters and a depth of about 100 millimeters to about 600 millimeters. In certain aspects of the invention, the methods comprise the further step of plugging the treatment hole(s).

In certain aspects of the invention, the disclosed methods further comprise the step of adding an accelerant to the treatment hole into which the solid body has been inserted. According to one aspect of the invention, the accelerant is selected from the group consisting of a copper compound and a zinc compound. According to one aspect of the invention, the product may comprise an accelerant, such as a compound, including but not limited to copper naphthenate, copper sulfate, copper carbonate, basic copper carbonate, copper hydroxide, cupric oxide, ammoniacal copper, copper-amine complexes, cuprous oxide, copper oxychloride, copper dimethyldithiocarbamate, copper borate or a zinc compound, including but not limited to zinc naphthenate. The accelerant may be in the form of a solid, dissolved liquid or copper particles dispersed in an aqueous or non-aqueous carrier. The wooden structures suitable for treatment by the disclosed methods include but are not limited to utility poles, pilings, timbers, and railroad ties.

The present invention also provides a method for manufacturing a product essentially free of water for internal remedial treatment of wood, comprising the steps of uniformly blending a mixture of dazomet, a lubricant, and a binder; and compressing the blended mixture into a solid body without the addition of water or aqueous solutions. In certain aspects of the invention, the dazomet is powdered or granulated and the lubricant is selected from the group consisting of magnesium stearate, aluminum stearate, calcium stearate, talc, sodium benzoate, glyceryl mono fatty acid, glyceryl monostearate, glyceryl dibehenate, glyceryl palmito-stearic ester, hydrogenated cotton seed oil, castor seed oil, and vinylpyrrolidone-vinyl acetate copolymer. In certain aspects of the invention, the binder is selected from the group consisting of maltodextrin, dextrin, pectin, starch, modified starch, and starch derivatives and the mixture contains from about 80 parts to about 99 parts dazomet, from about 0.5 parts to about 5 parts lubricant, and from about 0.5 parts to about 15 parts binder.

DETAILED DESCRIPTION OF THE INVENTION

Dazomet (3,5-dimethyl-1,3,5,-thiadiazinane-2-thione) is a cyclic dithiocarbamate biocide used in the control of fungi that functions by decomposing within wood to release MITC, the primary fungitoxic component. When exposed to wood or moist soils, solid dazomet decomposes into MITC, formaldehyde, carbon disulphide ($CS_2$), hydrogen sulphide ($H_2S$), and monethylamine, which interact together. MITC is the major product (approximately 98%) of dazomet decomposition, with a theoretical maximum decomposition rate for dazomet of approximately 45% (meaning that a 210 gram application of dazomet would yield the equivalent of 94.5 grams of MITC). The generation and dissipation of MITC from dazomet depends on chemical and physical factors, with the most critical factors being temperature, moisture and pH. In particular, MITC generation and dissipation increases at higher levels of temperature and moisture. Dazomet rapidly hydrolyses in water, with the rate of hydrolysis increasing at higher levels of pH. In wood, dazomet decomposes to release MITC at the stoichiometric conversion rate of approximately 45%.

A product for internal remedial treatment of wood, as well as towards the methods of using and manufacturing such a product, are disclosed herein. A product for internal remedial treatment of wood, comprising a solid body of dazomet is disclosed. Methods for internal remedial treatment of wood, comprising the step of inserting a solid body of dazomet into a treatment hole in a wooden structure are also disclosed. A method for manufacturing a product for internal remedial treatment of wood, comprising the steps of blending a mixture of dazomet, a lubricant, and a binder, and compressing the blended mixture into a solid body are disclosed.

In certain aspects disclosed herein, a product for the internal remedial treatment of wood comprises a solid body of dazomet that has been formed by compressing powdered dazomet or granular dazomet into a solid body.

As used herein, "solid body" refers to the form of the compressed compositions disclosed herein, including but not limited to rods, tablets, pellets and or sticks. In certain aspects, the solid body, as used herein, is a shaped body produced by compressing the compositions disclosed herein into a desired three-dimensional shape. In various aspects, the shaped body is selected from the group consisting of a rod, a tablet, a pellet, and a stick. In certain aspects, the shaped body is a rod. However, it would be readily apparent to those skilled in the art that the solid body of dazomet could be shaped into other forms as well. In one aspect, the rod has a diameter of between about 5 millimeters to about 30 millimeters, a length of between about 100 millimeters to about 6000 millimeters, and a weight of about 10 grams to about 5000 grams. It would be readily apparent to one skilled in the art, however, that the disclosure is not limited to these particular dimensions or shapes. In one aspect, the dimensions of the solid body of dazomet could be customized to a particular shape and set of dimensions specified by a customer.

As used herein, "sheathless" means no covering on the outermost surface of a solid body of the compositions disclosed herein, including but not limited to tubes, wrappers or coatings, including but not limited to metal, plastic or paper tubes, perforated tubes or perforated or gas permeable (MITC, for example) wrappers or coatings. The compositions disclosed herein may specifically exclude tubes, such as plastic, metal, or paper tubes, gas-permeable tubes, perforated tubes, gas permeable (MITC) wrappers, wrappings and coatings.

In certain aspects of the invention, the product for the internal remedial treatment of wood comprises a solvent. In preferred embodiments of the invention, the solvent is an aqueous solution. However, it would be readily apparent in the art that acetone or other organic solvents could be used. The water solubility of dazomet ranges between approximately 3.5 and 3.9 grams per liter at 20.2° C. and a pH of between 5 and 9. At 25° C., hydrolyzing dazomet has a half-life of approximately 6-10 hours at a pH of 5, 2-3.9 hours at a pH of 8, and 0.8-1 hours at a pH of 9. In moist, aerobic soil, the half-life of dazomet is less than 24 hours.

In certain aspects of the invention, the product for the internal remedial treatment of wood comprises an accelerant. Accelerants speed the decomposition of dazomet into MITC, increasing the rate of diffusion of the MITC in the wood. In aspects of the invention, the accelerant is selected from the group consisting of zinc naphthenate, liquid copper naphthenate, copper carbonate, copper hydroxide and copper sulfate powder. In a preferred embodiment of the invention, between about 10 and about 30 grams of liquid copper naphthenate solution are added to a treatment hole into which a solid body of dazomet has been inserted.

In aspects of the invention, a liquid copper naphthenate solution used as an accelerant may be made up of between about 0.1% and about 8% liquid copper by weight, and made be water-borne or oil-borne. In a preferred embodiment, the liquid copper naphthenate solution has a liquid copper concentration of about 1% to about 2%. Accelerants containing copper enhance the production of MITC by decomposing dazomet and reduce the evolution of carbon disulfide (which volatizes rapidly, leaving the wood unprotected). Additionally, some accelerants, such as copper sulfate, result in MITC production from dazomet even in the absence of moisture, so such accelerants should be kept separate from the dazomet until treatment begins or immediately prior to treatment.

The MITC produced by dazomet is effective in controlling wood fungi and can rapidly eradicate colonies of decay fungi in wooden structures, including brown-rot fungi, white-rot fungi, and soft-rot fungi. The approximate threshold range for MITC to be effective in combating wood-decay fungi is between about 20 and about 40 µg/g (ppm) of oven-dried wood sample. Long exposures of dazomet are effective in controlling fungal growth.

In aspects of the invention, the solid body is an insecticide and a nematicide. The MITC produced by dazomet is toxic to and effective in killing nematodes and insect pests such as army-worms, cut-worms, termites, beetles including powderpost beetles, and ants including carpenter ants. Due to dazomet's mode of application to wood, which prevents exposure to bees, the product is relatively non-toxic and harmless to bees such as honeybees. Additionally, while dazomet has initially strong effects on populations of soil-dwelling organisms such as earthworms and arthropods, these effects are reversible. The end products of dazomet's degradation after complete mineralization are bicarbonate, nitrate, and sulphate, which can be considered nutrients for plants.

A product for the internal remedial treatment of wood is applied to a wooden structure. In certain aspects disclosed herein, as disclosed herein, by inserting or dropping a solid body of the compositions disclosed herein into a treatment hole in a wooden structure. In certain embodiments, the wooden structure is a utility pole, piling, timber or railroad tie, but it would be readily apparent to one skilled in the art that the products disclosed herein may be applied to any type of wooden structure for the purposes of combating decay. It would be readily apparent to one skilled in the art that the products disclosed herein could be applied to all types and species of wood to combat internal decay.

In aspects disclosed herein, the treatment holes have been pre-drilled into the wooden structure. In other aspects of the present invention, methods of applying the solid body to a wooden structure comprise boring or drilling one or more treatment holes into the wooden structure. When boring treatment holes into a wooden structure, the utility pole, piling, or other type of wooden structure should be inspected thoroughly to determine an optimal drilling pattern that avoids metal fasteners, seasoning checks, and severely rotted wood.

In aspects of the invention, boring or drilling the one or more treatment holes into a utility pole or piling comprises drilling holes of between about 19 and about 22 mm (approximately ¾ to ⅞ inches) in diameter downwards at an angle of about 45° to about 60° through the center of the pole or pile. The length of the hole is approximately 2.5 times the radius of the pole or pile, with a minimum hole length of between 150 mm and 305 mm. Therefore, smaller structures with smaller radii may necessitate the use of a steeper drilling angle. In terrestrial piles, a first treatment hole is drilled or bored at or slightly below the ground line. One or more subsequent holes can then be drilled or bored higher on the pole or pile, moving up and around the pole or pile in a spiraling pattern. Depending on the size of the pole or pile, holes should be spaced at either approximately 90° or 120° around the pole or pile, with a vertical distance of between about 150 mm to about 325 mm (approximately 6 to 12 inches) between treatment holes near the groundline, with a vertical distance of about 275 mm to about 325 mm (approximately 12 inches) between treatment holes higher on the pole or pile. For aquatic poles or piles, at a minimum, the lowest part of a treatment hole should be above the waterline.

In other aspects of the invention, boring or drilling one or more treatment holes into large timbers or glued-laminate beams comprising boring or drilling holes into a narrow face of the member (usually either the top or bottom). Treatment holes can be bored or drilled straight down or up or slanted into these types of wooden structures. Slanting a treatment hole may be preferable, as it provides a larger surface area inside the holes for the escape of the MITC fumigant. As a rule, the holes should be extended to within about two inches (51 mm) of the top or bottom of the member, and should be no more than four feet (1.22 m) apart.

Fumigants should not be applied into voids or when application holes intersect voids or checks. This precaution limits the risk that the fumigant product will accidentally be released into the environment. Care should be taken in the removal of wooden structures that have been treated with the solid body, to ensure that the chemicals have moved out of the treatment hole and into the surrounding wood.

In certain aspects disclosed herein, once the solid body of dazomet has been inserted into a treatment hole, accelerant may be added to that treatment hole. As discussed above, possible accelerants may include copper or zinc compounds in liquid form, including dispersed particles, although it would be readily apparent to one skilled in the art that other copper- and zinc-containing compounds and other accelerants could be used as well. In certain embodiments of the invention, between about 10 grams and about 30 grams of accelerant are added to the treatment hole after the dazomet body has been inserted.

In certain aspects disclosed herein, the treatment hole is plugged after the solid body of dazomet (and, in certain aspects, accelerant) has been added to the treatment hole. The treatment hole may be plugged immediately after application of the product, and can be plugged with a tight-fitting treated wood dowel or a removable plastic plug, although it would be readily apparent to one skilled in the art that other methods of plugging the treatment hole could be used. There should be sufficient room in treatment hole for the plug to be driven in without squirting liquid chemical out of the hole or impacting the solid dazomet body.

By using a removable plug for plugging a treatment hole, additional dazomet treatments can be applied to the same treatment holes over the course of subsequent months and years. By utilizing a solid body of dazomet, as disclosed herein, a precise dose of fumigant can be easily reapplied to the one or more treatment holes in a wooden structure over subsequent treatment cycles by merely removing the plug and inserting a fresh solid body.

A product for the internal remedial treatment of wood is manufactured, as disclosed herein, by uniformly blending a mixture of dazomet, a lubricant, and a binder, and then compressing the blended mixture into a solid body. In certain embodiments, dazomet is powdered or granular, although it would be readily apparent to one skilled in the art that other forms of solid dazomet could be used.

In certain aspects disclosed herein, the disclosed compositions further comprise a lubricant. The lubricant is selected from the group consisting of magnesium stearate, aluminum stearate, calcium stearate, talc, sodium benzoate, glyceryl mono fatty acid, glyceryl monostearate, glyceryl dibehenate, glyceryl palmito-stearic ester, hydrogenated oils, hydrogenated cotton seed oil, hydrogenated castor seed oil, and vinylpyrrolidone-vinyl acetate copolymer. However, it would be readily apparent to one skilled in the art that other lubricants could be used.

In other embodiments, the disclosed compositions comprise a binder comprising a polysaccharide. In one embodiment, the polysaccharide is selected from the group consisting of maltodextrin, dextrin, pectin, starch, modified starch, and starch derivatives. However, it would be readily apparent to one skilled in the art that other binding agents could be used.

In one aspect of the invention, the binder is a carbohydrate, including, monosacharides, oligosaccharides and polysaccharide, including starches, dextrins, maltodextrins, soy flour, dextrose, a polyol or a combination thereof.

Suitable starches include granular starch and any starch that gelatinizes to produce a viscous colloidal solution with high binding power, upon heating in an aqueous environment. The viscosity, binding, flow, tackifying film-forming properties of a starch may be adjusted by selecting, modifying, and/or gelatinizing a starch according to methods known in the art.

Suitable dextrins include polysaccharides formed during pyrolysis of dry or acid-modified starches. Dextrins may be used at higher solids levels than native or modified starches, creating stronger bonds, more tack and faster-drying properties than pastes made from unmodified starch.

Soy flour, a co-product that remains after oil is extracted from soybeans. Soy flour requires less drying time, uses less water and produces less waste than conventional glues.

Maltodextrins are glucose polymeric chains with a molecular weight between that of starch and a glucose syrup. Maltodextrins are highly water soluble and are available both in powder and liquid form.

Dextrose is the fundamental monomer of all starch-based products and may be used in liquid, granular, powder or crystalline form.

Polyols include but are not limited to sorbitol, maltitol, mannitol, xylitol, erythritol isomalt and isosorbide.

In one aspect of the invention, the binder is a monosaccharide, such as glucose or another monosaccharide, such as a monosaccharide or glucose syrup.

In certain aspects disclosed herein, the mixture contains from about 80 parts to about 99 parts dazomet, from about 0.25 parts to 5 parts lubricant, and from about 0.5 parts to 15 parts binder. In a preferred embodiment, the mixture contains at least 97 parts dazomet. However, it would be readily apparent to one skilled in the art that the proportions of the ingredients of the mixture could differ, and that additional ingredients, including but not limited to a filler, could be added.

In certain aspects disclosed herein, the mixture is formed by blending until the composition is uniform. Blending may be accomplished by using a blender selected from the group consisting of V-blenders, double cone blenders, vertical blenders, and ribbon blenders. It would be readily apparent to one skilled in the art, however, that other devices could be utilized.

In embodiments of the present invention, the mixture is blended for at least 3 minutes, at least 5 minutes, at least 10 minutes, and at least 20 minutes.

In certain aspects disclosed herein, the mixture is compressed into a solid body essentially free of water. As used herein, "essentially free of water" means a solid body of powdered or granular dazomet to which no water has been added during manufacture. A solid body, essentially free of water, ensures that the dazomet remains stable and does not significantly decompose, until application.

In certain aspects, as disclosed herein, the mixture is compressed using either a single-punch tablet press or a rotary tablet press, although it would be readily apparent to one skilled in the art that other devices could be used.

EXAMPLES

The following Examples are only illustrative and are not intended to limit the scope of the invention in any manner. It will be readily seen by one of ordinary skill in the art that the present invention fulfills all of the objectives set forth above. It is therefore intended that the protection granted herein be limited only by the definition contained in the appended claims and equivalents thereof.

Example 1

Preparation of a Dazomet Composition

A wood preservative composition comprising dazomet (98% Tetrahydro-3,5-dimethyl-2H-1,3,5-thiadiazine-2- thione) was prepared from 97.00 parts of granular dazomet, 1.00 parts Lubritab, a hydrogenated vegetable oil, and 2.00 parts Maltrin M-200 a maltodextrin. The components were mixed until evenly dispersed. The resulting blend was free flowing and did not clump or cake.

Example 2

Preparation of a Dazomet Composition

A wood preservative composition comprising dazomet (98% Tetrahydro-3,5-dimethyl-2H-1,3,5-thiadiazine-2-thione) was prepared from 97.50 parts of granular dazomet, 0.50 parts Lubritab, a hydrogenated vegetable oil, and 2.00 parts Maltrin M-200 a maltodextrin. The components were mixed until evenly dispersed. The resulting blend was free flowing and did not clump or cake.

Example 3

Preparation of a Dazomet Composition

A wood preservative composition comprising dazomet (98% Tetrahydro-3,5-dimethyl-2H-1,3,5-thiadiazine-2-thione) was prepared from 95.00 parts of granular dazomet, 1.00 parts Lubritab, a hydrogenated vegetable oil, and 4.00 parts Maltrin M-200 a maltodextrin. The components were mixed until evenly dispersed. The resulting blend was free flowing and did not clump or cake.

Example 4

Compression of a Dazomet Composition

The blended composition prepared in Example 1 was used to form a solid body of dazomet. The mixture was compressed under pressure using a Stokes Model T-4, 12-ton dual motion ceramic compacting press. To form the tablet or rod, the blended formulation was metered into a cavity formed by two punches and a die, and then the punches were compressed to fuse the material. After compression, the lower punch was raised to eject the tablet or rod. The resulting tablets or rods had good hardness and friability and were resistant to picking and sticking to the punch faces. The resulting tablets were uniform in weight or density and showed no signs of defects such as laminating or chipping. The finished tablets or rods, measured approximately 3 inches in length with a diameter of about one half-inch.

Example 5

Compression of a Dazomet Composition

The blended composition prepared in Example 2 was used to form a solid body of dazomet. The mixture was compressed under pressure using a Stokes Model T-4, 12-ton dual motion ceramic compacting press. To form the tablet or rods, the blended formulation was metered into a cavity formed by two punches and a die, and then the punches were pressed together with great force to fuse the material together. After compression, the lower punch was raised to eject the tablet or rod. The resulting tablets or rods had good hardness and friability and were resistant to picking and sticking to the punch faces. The resulting tablets were uniform in weight or density and showed no signs of defects such as laminating or chipping. The finished tablets or rods, measured approximately 1.5 inches in length with a diameter of about 5/16 of an inch.

Example 6

Compression of a Dazomet Composition

The blended composition prepared in Example 3 was used to form a solid body of dazomet. The mixture was compressed under pressure using a Stokes Model T-4, 12-ton dual motion ceramic compacting press. To form the tablet or rod, the blended formulation was metered into a cavity formed by two punches and a die, and then the punches were pressed together with great force to fuse the material together. After compression, the lower punch was raised to eject the tablet or rod. The resulting tablets or rods had good hardness and friability and were resistant to picking and sticking to the punch faces. The resulting tablets were uniform in weight or density and showed no signs of defects such as laminating or chipping. The finished tablets, or rods, measured approximately 1.5 inches in length with a diameter of about one 5/16 of an inch.

What is claimed is:

1. A composition comprising
   a flowable mixture of
      between 93% and 96% solid tetrahydro-3,5-dimethyl-2H-1,3,5-thiadiazine-2-thione, by weight of the composition;
      between 0.5% and 5.0% of a saturated oil, by weight of the composition; and
      between 1% and 5% of a polysaccharide, by weight of the composition.

2. The composition of claim 1, wherein the solid tetrahydro-3,5-dimethyl-2H-1,3,5-thiadiazine-2-thione is in the form of granules or a powder.

3. The composition of claim 1, wherein the saturated oil is a hydrogenated oil.

4. The composition of claim 3, wherein the saturated oil is a hydrogenated vegetable oil.

5. The composition of claim 1, wherein the polysaccharide is a starch.

6. The composition of claim 5, wherein the starch is a maltodexrin.

7. The composition of claim 1, wherein the composition is water-free.

8. A product for internal remedial treatment of wood consisting of
   a sheathless rod of a compressed dazomet composition,
   wherein the dazomet composition consists of
      between 90% and 96% solid tetrahydro-3,5-dimethyl-2H-1,3,5-thiadiazine-2-thione, by weight of the composition;
      between 0.5% and 5.0% of a saturated oil, by weight of the composition;
      between 1% and 5% of a polysaccharide, by weight of the composition;
      and
      an accelerant;
   wherein the rod has a length of about 100 millimeters to about 350 millimeters; and
   wherein the dazomet composition is flowable before compression.

9. The product of claim 8, wherein the rod has a diameter of about 5 millimeters to about 30 millimeters.

10. The product of claim 8, wherein the rod has a weight of between 10 grams and 500 grams.

11. The product of claim 8, wherein the accelerant is selected from the group consisting of copper naphthenate, copper sulfate, copper carbonate, basic copper carbonate, copper hydroxide, cupric oxide, cuprous oxide, copper oxychloride, copper dimethyldithiocarbamate, copper borate and zinc naphthenate.

12. The product of claim 8, wherein the solid tetrahydro-3,5-dimethyl-2H-1,3,5-thiadiazine-2-thione is in the form of granules or a powder.

13. The product of claim 8, wherein the saturated oil is a hydrogenated oil.

14. The product of claim 13, wherein the saturated oil is a hydrogenated vegetable oil.

15. The product of claim 8, wherein the polysaccharide is a starch.

16. The product of claim 15, wherein the starch is a maltodexrin.

17. The product of claim 8, wherein the dazomet composition comprises between 93% and 96% solid tetrahydro-3,5-dimethyl-2H-1,3,5-thiadiazine-2-thione, by weight of the composition.

18. A flowable mixture consisting of
    between 90% and 96% solid dazomet, by weight of the composition;
    between 0.5% and 5% of a saturated oil, by weight of the composition; and
    between 1% and 5% of a polysaccharide, by weight of the composition.

19. The composition of claim 18, wherein the solid dazomet comprises tetrahydro-3,5-dimethyl-2H-1,3,5-thiadiazine-2-thione in the form of granules or a powder.

20. The composition of claim 19, wherein the hydrogenated oil comprises a hydrogenated vegetable oil.

21. The composition of claim 18, wherein the saturated oil is a hydrogenated oil.

22. The composition of claim 18, wherein the polysaccharide is a starch.

23. The composition of claim 22, wherein the starch comprises maltodexrin.

24. A product for internal remedial treatment of wood comprising the composition of claim 18 compressed into a solid body.

25. The product of claim 24, wherein the solid body is a rod.

26. The product of claim 25, wherein the rod has a diameter of about 5 millimeters to about 30 millimeters, and a length of about 100 millimeters to about 350 millimeters.

27. The product of claim 25, wherein the rod has a weight of between 10 grams and 500 grams.

28. The product of claim 24, wherein the product is sheathless.

* * * * *